(12) United States Patent
Porter et al.

(10) Patent No.: US 11,581,074 B2
(45) Date of Patent: Feb. 14, 2023

(54) WHISKER AND PAW WEB APPLICATION

(71) Applicant: THE ON-DEMAND PET INC, La Jolla, CA (US)

(72) Inventors: Patricia Porter, San Diego, CA (US); Patricia Gigliotti, San Diego, CA (US); Alina Adon, San Diego, CA (US)

(*) Notice: Subject to any disclaimer, the term of this patent is extended or adjusted under 35 U.S.C. 154(b) by 0 days.

(21) Appl. No.: 16/825,260

(22) Filed: Mar. 20, 2020

(65) Prior Publication Data
US 2022/0051764 A1 Feb. 17, 2022

(51) Int. Cl.
G16H 10/60 (2018.01)
G16H 50/20 (2018.01)
G08B 5/22 (2006.01)
G06F 40/40 (2020.01)
G06N 5/022 (2023.01)

(52) U.S. Cl.
CPC ............ G16H 10/60 (2018.01); G06F 40/40 (2020.01); G06N 5/022 (2013.01); G08B 5/22 (2013.01); G16H 50/20 (2018.01)

(58) Field of Classification Search
CPC ........ G16H 10/60; G16H 50/20; G06F 40/40; G06N 5/022; G08B 5/22
USPC ....................................................... 705/2–3
See application file for complete search history.

(56) References Cited

U.S. PATENT DOCUMENTS

| 5,301,105 | A | | 4/1994 | Cummings | |
|---|---|---|---|---|---|
| 6,047,259 | A | * | 4/2000 | Campbell | G16H 15/00 705/2 |
| 7,613,620 | B2 | | 11/2009 | Salwan | |
| 7,716,072 | B1 | | 5/2010 | Green | |
| 7,991,485 | B2 | | 8/2011 | Zakim | |
| 8,000,979 | B2 | | 8/2011 | Blom | |
| 8,126,739 | B2 | | 2/2012 | Green | |
| 2002/0029157 | A1 | | 3/2002 | Marchosky | |
| 2003/0212574 | A1 | * | 11/2003 | Olivier | G06Q 30/02 705/2 |
| 2004/0019501 | A1 | | 1/2004 | White | |
| 2005/0027567 | A1 | | 2/2005 | Taha | |
| 2005/0108052 | A1 | | 5/2005 | Omaboe | |
| 2005/0187796 | A1 | | 8/2005 | Lee | |
| 2006/0106641 | A1 | | 5/2006 | Bartsch | |
| 2006/0282302 | A1 | | 12/2006 | Hussain | |
| 2007/0282654 | A1 | | 12/2007 | Sarkar | |
| 2009/0177495 | A1 | | 7/2009 | Abousy | |
| 2009/0259493 | A1 | * | 10/2009 | Venon | G16H 20/10 705/3 |
| 2010/0076786 | A1 | | 3/2010 | Dalton | |
| 2010/0082369 | A1 | | 4/2010 | Prenelus | |
| 2011/0099024 | A1 | | 4/2011 | Lee | |

(Continued)

FOREIGN PATENT DOCUMENTS

WO 2001069513 9/2001

Primary Examiner — Michael Tomaszewski
(74) Attorney, Agent, or Firm — Buche & Associates, P.C.; John K. Buche; Bryce A. Johnson

(57) ABSTRACT

Methods and apparatus of a smart electronic health records platform for veterinarians and human providers are disclosed. The platform integrates clinical IT systems with patient tracking whiteboards, billing processes and artificial intelligence software to increase efficiency of the patient treatment process. By aggregating many services into one platform, interaction and communication between clinics and patients will be enhanced and streamlined.

12 Claims, 12 Drawing Sheets

(56) References Cited

U.S. PATENT DOCUMENTS

| | | | |
|---|---|---|---|
| 2013/0218592 A1* | 8/2013 | Hashmat | G06F 21/6245 705/3 |
| 2014/0019128 A1* | 1/2014 | Riskin | G16H 10/60 704/235 |
| 2014/0052463 A1* | 2/2014 | Cashman | G06Q 10/1095 705/2 |
| 2017/0161450 A1* | 6/2017 | White | G16H 40/67 |
| 2017/0270257 A1 | 9/2017 | Clair | |
| 2020/0381119 A1* | 12/2020 | Gibbs | G16H 40/67 |

\* cited by examiner

WHISKER AND PAW WEB APPLICATION

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of Invention

The disclosure relates to computer systems and electronic medical records for veterinarians, patient care processes, web applications, health tracking, and artificial intelligence driven recommendation or diagnosis engines.

2. Background

A smooth patient treatment process for pets is a multistep process that demands cohesion between clinical staff, medical practitioners, and patients. The process varies between clinics, but generally follows the same path. Appointments to see medical providers are scheduled.

Patients, in this case pets, arrive and are received by the clinic. A medical assistant gathers information and measurements which are relayed to all relevant parties. One of whom, generally the veterinarian, makes a diagnosis and maps a treatment in hopes of resolving the medical issue. The veterinarian explains the treatment to the pet owner. Shortly after, the business office processes the client's insurance claims, and either bills the client's insurance or bills the client. Once the bill is paid, the client and their pet is sent on their way.

Although these processes sound simple, they become difficult to maintain when many patients are being treated simultaneously. To remain efficient individuals who curate and oversee these processes should put substantial effort into making their processes work well. Specifically, the patient treatment process requires organization, fast and accurate decision making, and proper information distribution. If the attributes outlined are present, a veterinary clinic will operate more efficiently. Ideally, patients will have little or no wait times between each step of the process. Pertinent information will be completely disclosed to all parties. Veterinarians will make proper diagnoses fast. Insurance will get billed appropriately. And, patients will leave the clinic knowing exactly what steps they must take to treat their pet.

Unfortunately, inefficiencies are inherently present in nearly every process. Some inefficiencies are unavoidable. Others may be minimized. Some may be completely negated by strategic practices. The attributes that dictate process efficiency such as the level of skill of practitioners, clinical organization, proper billing coding, and process complexity varies from clinic to clinic, day to day. On days with many pet owners or days where clinics are short staffed, process efficiency will likely decrease. Some clinics have very low average efficiency, while others have a higher average process efficiency. Although efficiency is dependent on many factors, it is reasonably dependent on clinical information technology systems and electronic medical records.

Electronic medical records are a systematized collection of patient health information in a digital format. These records are a keystone of the patient treatment process because decisions about diagnoses, billing codes, and treatment plans are heavily reliant on the information stored in these records. Further, the distribution of these records in real time to all parties in need of knowing is important to maintaining high levels of operational efficiency in the patient care process. However, the distribution and transfer of these records from party to party is often made difficult by a myriad of incongruent information technology systems and workflow practices in veterinary clinics. More specifically, electronic medical records are not always properly integrated with clinical note taking systems, scheduling, patient tracking tools (e.g., handwritten notes on whiteboards), email, and billing. Because these systems and practices may not be properly integrated, they lack synergy and lead to process inefficiencies.

Not all process efficiencies stem from information technology systems or electronic medical records. Other process inefficiencies can be attributed to differential diagnosis. Often, practitioners must differentiate between two or more conditions which share similar signs or symptoms. When faced with differential diagnosis veterinarians are required to manually look up differential diagnosis through the Veterinary Advisor textbook, other electronic databases, and their own practical veterinarian knowledgebase.

Manually looking up differential diagnosis can become very time consuming. Time consumption due to this step of the process is often contingent upon the level of skill and experience of the veterinarian. Since veterinarians are often already pressed for time, time lost to differential diagnosis leads the entire patient treatment process to slow down.

Almost all parties involved in the patient treatment process can suffer from these inefficiencies. Patient treatment process inefficiencies effect veterinary clinics of every size and type, in some way. Although some of these efficiencies are unavoidable, some are potentially easily improved because they are related to the unification of parties involved and their different information technology systems. For example, with more efficient diagnosis, billing administrators can obtain the correct diagnosis code and match it to the correct diagnostic code which is typically tedious for medical billers and often leads to delays and inaccuracies. Other inefficiencies can be attributed to the rote and tedious elements of working as a veterinarian.

The majority of these information technology systems were not designed for veterinary clinics or integration with other information technology systems. Thus, a need exists for a platform which integrates these systems and is designed to streamline and automate parts of the veterinary care process.

One proposed solution to the identified need is disclosed in U.S. Pat. Application No. 20110099024A1 (published Apr. 28, 2011 and hereinafter "healthcare management system"). Specifically, the healthcare management system disclosed in that document may comprise, a computer database for maintaining personal and medical records of a patient, means for remotely accessing the database by a medical provider, records of personal and medical information entered into the database by the provider, and an algorithm program for relating a diagnosed medical condition of the patient and at least one medical care action relating to the patient. The healthcare management system is not entirely satisfactory in view of the above identified need because (1) the system does not feature a platform for both patients and practitioners, (2) the system does not integrate all features of the patient care process, and (3) the system does not feature an artificial intelligence feature for differential diagnosis which employs a preprogrammed learning veterinary database which is linked to the billing parameters that allow timely processing of insurance and billing claims. Accordingly, there remains a need a smart electronic medical records platform which (a) integrates the information technology systems of the patient care process, (b) automates parts of the veterinary care process, and (c) automatically bills and closes patient billing records in coordination with insurance payers.

Other related art:

US20090177495A1 by Abousy (circa 2007) discloses a, "System, method, and device for personal medical care, intelligent analysis, and diagnosis;"

US20050108052A1 by Omaboe (circa 2004) discloses a, "Process for diagnostic system and method applying artificial intelligence techniques to a patient medical record and that combines customer relationship management (CRM) and enterprise resource planning (ERP) software in a revolutionary way to provide a unique- and uniquely powerful and easy-to-use-tool to manage veterinary or human medical clinics and hospitals;"

U.S. Pat. No. 8,000,979B2 by Blom (circa 2005) discloses an, "Automated patient management system;"

US20110099024A1 by Lee (circa 2009) discloses a, "Healthcare management system;"

US20050187796A1 by Rosenfeld (circa 2005) discloses a, "System and method for displaying a health status of hospitalized patients;"

U.S. Pat. No. 7,613,620 by Salwan (circa 2009) discloses, "Physician to patient network system for real-time electronic communications and transfer of patient health information;"

U.S. Pat. No. 7,991,485B2 by Zakim (circa 2007) discloses, "System and method for obtaining, processing and evaluating patient information for diagnosing disease and selecting treatment;"

WO2001069513A2 by Zakim (circa 2001) discloses, "A system and method for obtaining, processing and evaluating patient information for diagnosing disease and selecting treatment;"

US20020029157A1 by Marchosky (circa 2001) discloses a, "Patient-controlled automated medical record, diagnosis, and treatment system and method;"

US20060282302A1 by Hussain (circa 2006) discloses a, "System and method for managing healthcare work flow;"

US20040019501A1 by White (circa 2004) discloses a," Patient scheduling, tracking and status system;" US20070282654A1 by Sarkar (circa 2006) discloses, "Appointment scheduling system;"

U.S. Pat. No. 7,716,072B1 by Green (circa 2007) discloses an, "Integrated medical software system;"

US20060106641A1 by Bartsch (circa 2005) discloses a, "Portable task management system for healthcare and other uses;"

US20100076786A1 by Dalton (circa 2009) discloses, "Computer System and Computer-Implemented Method for Providing Personalized Health Information for Multiple Patients and Caregivers;"

US20050027567A1 by Taha (circa 2005) discloses, "System and method for health care data collection and management;"

U.S. Pat. No. 8,126,739B2 by Green (circa 2007) discloses a, "Method and system for tracking treatment of patients in a health services environment;"

US20170270257A1 by Clair (circa 2017) discloses, "System and method for health care data integration and management;"

US20100082369A1 by Prenelus (circa 2008) discloses, "Systems and Methods for Interconnected Personalized Digital Health Services;" and, U.S. Pat. No. 5,301,105A by Cummings (circa 1994) discloses, "All care health management system."

SUMMARY OF THE INVENTION

In view of the foregoing, it is an object of this application to disclose systems and methods of a smart electronic medical records (EMR) web application platform. The platform is designed to streamline and automate parts of the veterinary care process by incorporating smart recommendation engines from patient check in, to check out. Further, the application allows for patients to move through the patient care process in a more coherent manner by integrating different information technology systems. In addition, the application allows for communication and distribution of medical records and related information to patients and clinicians. Further, the platform allows for the automation of health care patient processes such as facets of Subjective, Objective, Assessment and Plan (SOAP) note taking and differential diagnosis. Lastly, the platform incorporates all the necessary medical billing functions to automap diagnosis codes to diagnostic codes for more efficient medical billing.

In an exemplary embodiment, the platform is preferably a smart veterinarian's electronic assistant (VEA). Suitably, the system may be a series of web pages which may be accessed via phone or computer via website or mobile application. The platform may integrate features such as scheduling, clinical note taking (SOAP method notes), billing, email reminders, patient tracking tools, dictation, recommendation engine (VEA, Google assistant® powered symptom and treatment mapping), medication administration, chatbots, and a patient and vet portal on to one application for both clinicians and patients. This aggregation of services into one artificial intelligence driven application intends to facilitate communication between all parties in the patient care process to yield efficient workflows.

In the preferred embodiment, the subject matter teaches recommendation engines to lower the cognitive demands put on clinicians and administration teams. The use of recommendation engines increases efficiency by automating the process for differential diagnosis and treatment plans to help clinicians provide solutions to routine issues faster. Faster solutions will increase patient care process efficiency by giving veterinarians more ample time.

The recommendation engine or veterinarian's electronic assistant, called VEA, powered by Google Assistant®, is focused on automating treatment plans, medical billing, and coding. VEA may be voice activated and this feature automates documentation generation. VEA may also use application programming interfaces or APIs such as natural language process, context analysis, a comprehensive symptom library, and image recognition to connect symptoms, diagnoses, treatments, billing, and coding. Further, VEA is designed to automatically suggest diagnostics and treatment paths with a built-in library of symptoms and treatment workflows. These workflows may suitably have been developed from the Veterinarian Advisor textbook, other electronic databases, and practical veterinarian knowledgebase. Suitably, VEA learns user habits every time a veterinarian or medical practitioner interacts with the platform, for continuous improvement to the recommendation software. VEA may also provide a smart, predictive recommendation engine that allows for automation around differential diagnosis. Additionally, VEA can automatically map treatment paths from symptoms, through diagnosis, to billing. Further, VEA demonstrates a full understanding of every potential diagnosis to clinicians.

In a preferred embodiment, automating these rote elements of the patient care process allows veterinarians to put more effort into solving more pressing problems for pets and their owners, while providing a higher standard of care. Similarly, VEA's automation capabilities aid the business office in facilitating an automated coding system that reduces billing errors and enables the office to submit claims to insurance much faster than prior art methods. Business office staff are simply required to identify the diagnosis code, then VEA automatically recognizes the appropriate diagnostic codes, and produces a claim that billing administrators can submit to insurance companies for payment.

Preferably, VEA mitigates post-visit note backlog because note taking is electronically available in the clinical note taking SOAP portal. This leads note-taking and treatment building to happen automatically through the VEA recommendation engine. VEA maps the treatment process and billing from symptoms to checkout. This allows veterinarians to avoid post-visit clinic note backlog, which stems from veterinarians needing to copy pen and paper notes to the computer at the end of the day. Avoiding this note backlog further increases process efficiency of the patient treatment process.

The application is also focused on guiding workflows. Workflows are managed by the whiteboard which is where all client and patient activities, such as appointments, reservations, check-ins, billing, and activities, are controlled. Workflows are guided by integrating interactive digital whiteboards with alerts. Whiteboards are further integrated with the entire EMR platform to ensure patients move efficiently through the treatment process. The application features built in workflows and dependencies which alert each member of the operation to perform their job duties in quick succession. Once an action is complete, the application will alert clinicians to begin the next step of the process. The digital whiteboard system allows for faster treatment time, higher levels of organization, and better continuity of care.

In other preferred modes, the application also accounts for billing and scheduling. It allows practitioners to create a package of wellness treatments at a set price, collect payments, and manage appointments throughout the year. The application automates billing, medical billing coding, and claims processing. Further, the application stores financial data, and integrates with prior art accounting systems.

The application could also suitably allow for increased interaction between patient and practitioner via a digital profile. The digital profile keeps all client records and increased clinic output with the calendar planning guide and automated reminders using multiple triggers from appointments and products. To further facilitate communication, the platform allows for appointment reminders and custom template messages to clients. Clients and practitioners may also receive responses through the platform.

BRIEF DESCRIPTION OF THE FIGURES

The manner in which these objectives and other desirable characteristics can be obtained is further explained in the following description and attached figures in which.

Figure 1:
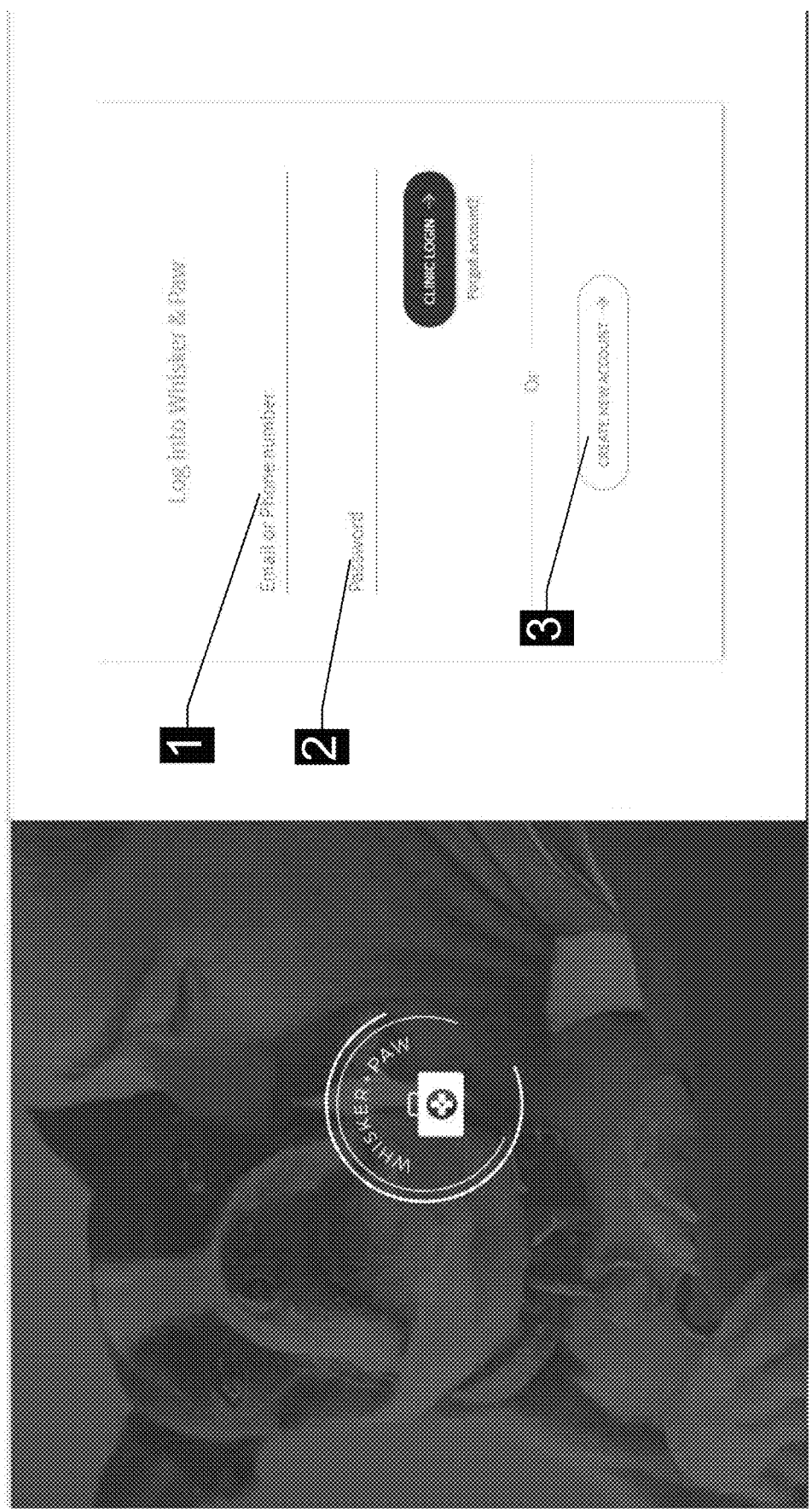
FIG. 1 is a preferable user interface for a user to log in to the platform.

It is to be noted, however, that the appended figures illustrate only typical embodiments disclosed in this application, and therefore, are not to be considered limiting of its scope, for the invention may admit to other equally effective embodiments that will be appreciated by those reasonably skilled in the relevant arts. The components in the figures are not necessarily to scale, with an emphasis instead being placed upon illustrating the principles of the invention. In the figures, like reference numerals designate corresponding parts throughout the different views.

DETAILED DESCRIPTION OF PROFFERED EMBODIMENTS

This disclosure describes preferred embodiments of web and application pages of a digital platform which integrates information technology systems and is designed to streamline and automate parts of the medical care process with a focus on veterinarian cases. This subject matter of this disclosure could also be applied to other medical situations, including for traditional medical care of humans. In this cases, the disclosed platform is described as a veterinarians' electronic assistant (VEA). In a preferred embodiment, a user of the platform system may create an account, which is associated with an email address or phone number, and a password. Suitably, the account may be accessed by the user via an email and password, which provides the user with an interface for managing, among other things, communications with the clinic, treatments plans, payment, and personal information. A medical practitioner may also log in to the platform to share information about the pet with other staff of the clinic, to map treatments, or manage the patient treatment process. A practitioner may also use VEA through the platform to access veterinary knowledge to resolve differential diagnoses. Clinic administrators may, among other things, log in to the platform to schedule appointments, manage billing, communicate with staff or pet owners, receive authorization, or alert staff that a patient has arrived.

The disclosed platform could be a series of web pages with unique artificial intelligent functionalities. The web pages are preferably defined by programming code on computer readable memory. Any design methodology may be utilized to implement a design for embodiments of the web pages, including but not limited to, object oriented design. Any programming language may be utilized to implement the program code of the web pages including any high level language, assembly language, or microcode.

FIG. 1 is a preferable user interface for a user to log in to the platform. In one mode of use, the user interface of FIG. 1 is the first page a user of the application may see when using the system. This page may be a precursor to the application's first use, which may be for managing appointments. To manage appointments, the pet owner may download the related web application. As shown, a user may be prompted to login by the login page which different parties may use to login, and which is shown in a preferred embodiment by FIG. 1. As shown one may login by entering either an email account or phone number into a username field 1 and a password into a password field 2. If one does not yet have an account a user may press a create new account button 3. As discussed later in connection with the other user interface screens and figures, after either logging in or creating an account, the pet owner may schedule an appointment for their pet's medical problems. This appointment may be automatically added to the pet owner's native calendar web application.

Appointment reminders may be sent automatically at some customizable time before the appointment, via text or email.

It is worth noting that the application is not a necessity for pet owners to have. The platform still has utility for clinics even if pet owners do not have the application. In the event that the pet owner does not have the application, she may simply call the clinic to schedule an appointment. The clinic staff may open up a calendar and schedule an appointment. Email or text reminders still may be sent to the owner. Then, the pet owner may add the event to their native calendar manually.

In another preferred mode, the application also allows users or clinic administrators to easily cancel appointments within the application. If both the owner and the administrator have the application, either may simply click cancel, and the appointment will clear from both the clinic's schedule and the owner's calendar application. If the owner does not have the application they may cancel their appointment by calling the clinic administrator. The administrator then may pull up the application, clicks cancel, then the appointment is removed automatically from the calendar, and time-slot is now open.

The schedule is available to all platform users on the clinic side. This availability may be accomplished via coupling the application into a database of schedules. This allows the clinic staff to pre-plan and review an upcoming schedule. The blocked schedule format may allow for easy scheduling because employee's days off, holidays, and lunches may be pre-blocked in the system.

Figure 2:
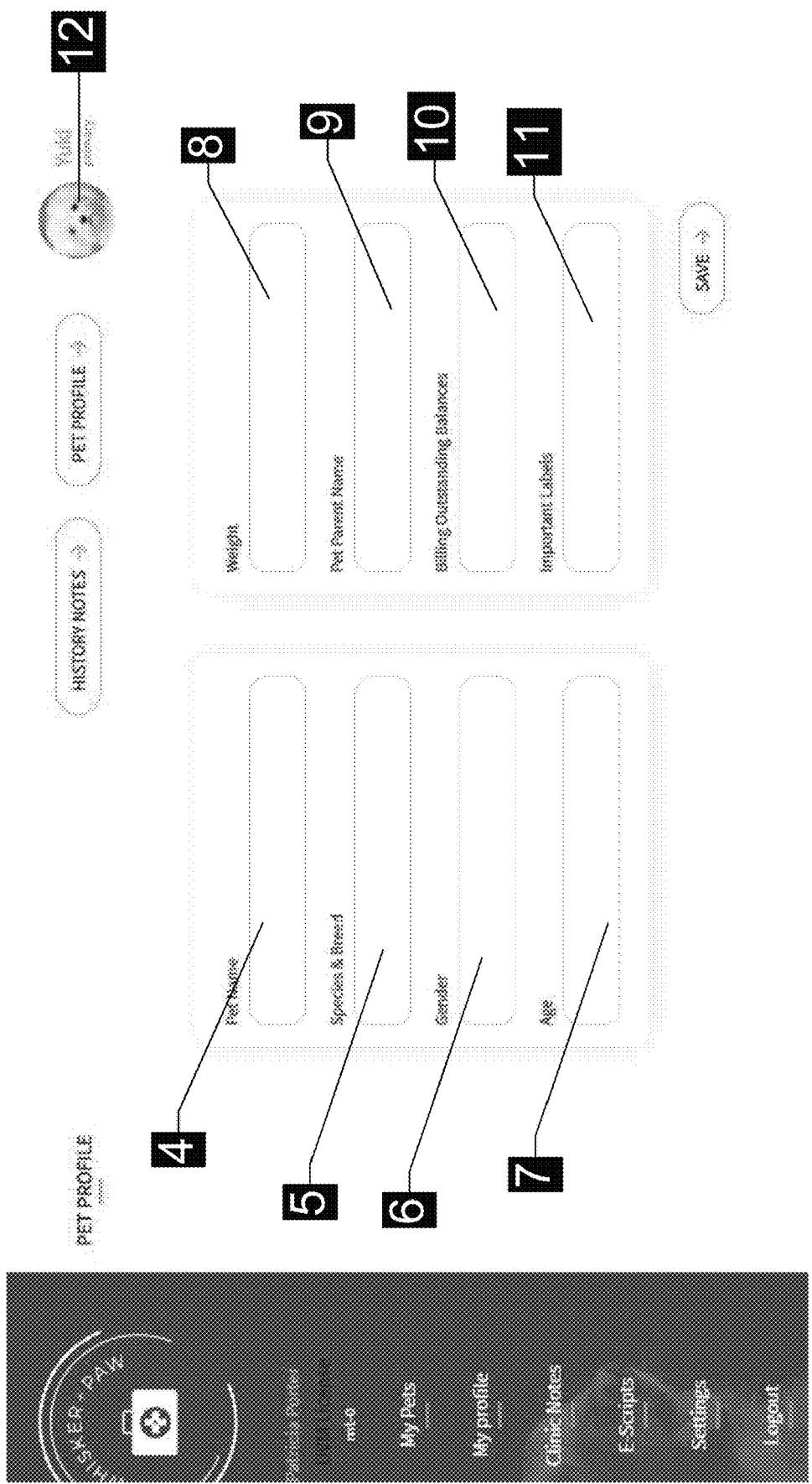
FIG. 2 is a part of a preferable user interface for a nurse to input pet information.

FIG. 2 shows a preferable user interface for a pet profile. Pet information such as pet name, species, gender, age, weight, parent name, labels, and outstanding balances are available or editable by using a pet name field 4, species field 5, gender field 6, age field 7, weight field 8, parent name field 9, labels field 10, and outstanding balance field 11. The specific pet profile is identified by the profile identifier 12. Once entered, the information may suitably be kept in a database that associates the pet profile with the particular account information.

Figure 3:
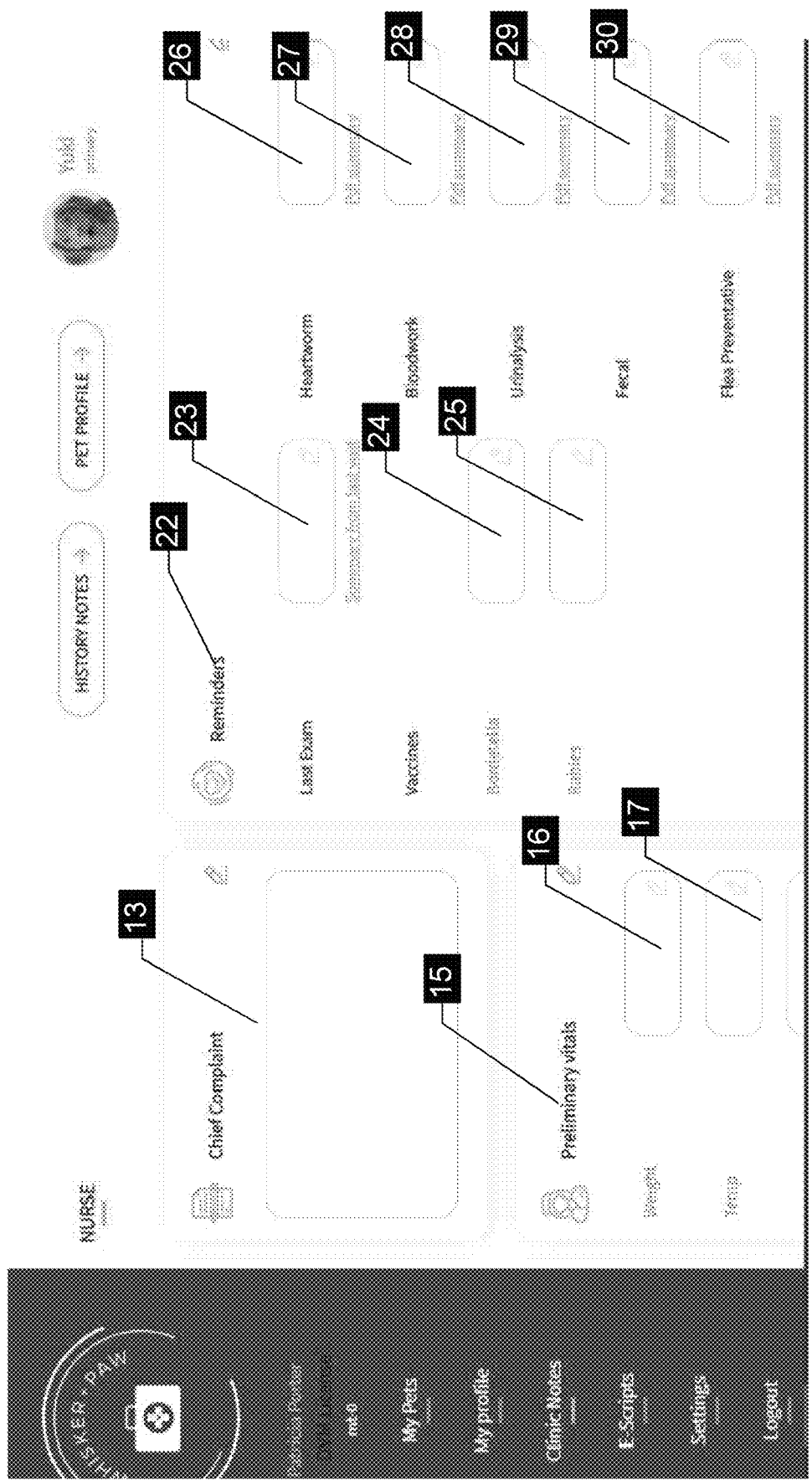
FIG. 3 is a preferable user interface for a nurse or technician to collect initial info, vitals, and confirm medical history prior to the veterinarian entering the exam room.
Figure 4:
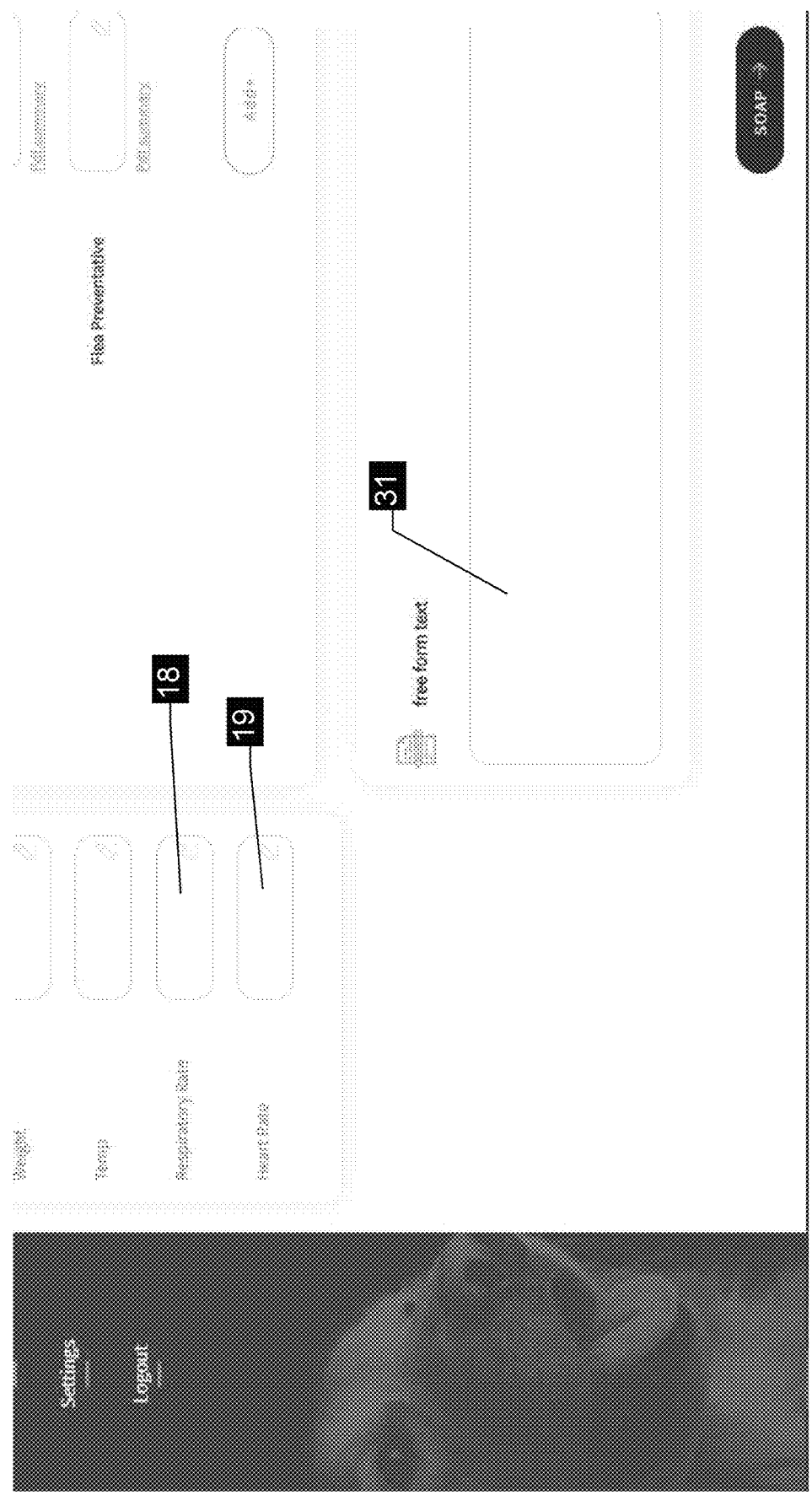
FIG. 4 is a part of a preferable user interface for a nurse to input pet information.

FIGS. 2 through 4 also show the applications first purposes when the pet owner and their pet first walk into the clinic to check-in to their appointment. Suitably, a computer or other computerized device may be made available to the nurse at the clinic. In one example, the clinic administrator greets the pet owner, welcomes them to sign in, and then escorts them to an exam room. The administrator may (on the computer or computerized device) navigate to the pet profile page of the application, as shown by FIG. 2. This page contains basic information about the pet owner and pet such as, but not limited to, outstanding balances, name of pet, name of pet parent, pet weight, pet gender, and pet age, among others.

FIGS. 3 and 4 show a preferable user interface for a nurse to input information. The administrator then may pull up the application on a tablet and open up the nurse section shown in FIGS. 3 and 4, to review or update all of the pet's vitals and medical history. Information regarding chief complaint may be entered in free form style into the chief complaint field 13. Under the preliminary vitals section 15 there are a plurality of fields to input information into, such as a weight field 16, a temperature field 17, a respiratory rate field 18, and a heart rate field 19. Under the reminders section 22, a nurse may input information into a last exam field 23, heartworm field 26, bloodwork field 27, urinalysis field 28, fecal field 29, flea preventative field 30, and free form text field 31. After review or edit, the clinic administrator may update the patient status to "DVM ready" which means that the veterinarian is notified, via the whiteboard view, that pet owner and their pet are ready to see the veterinarian.

Figure 5:
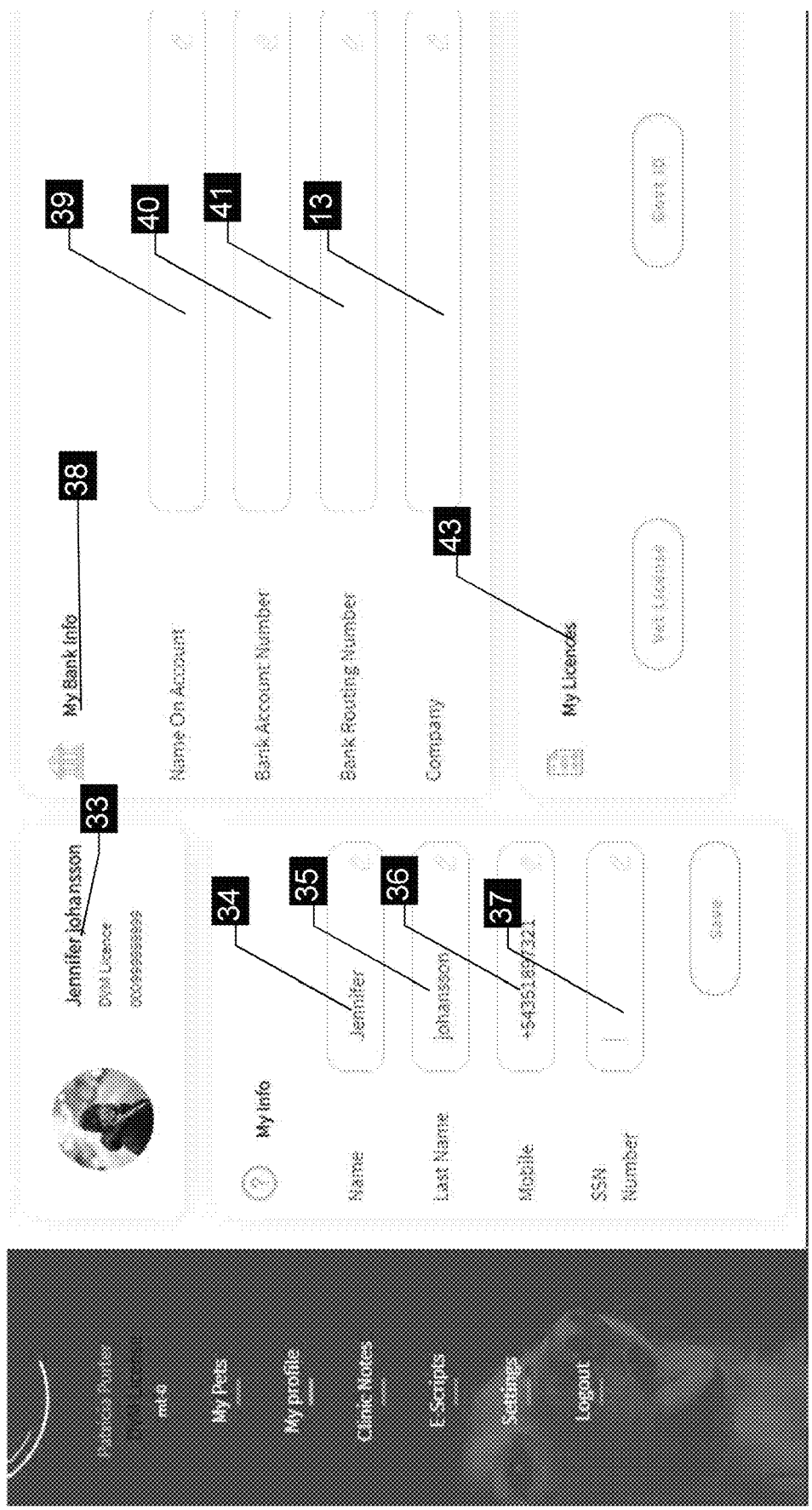
FIG. 5 is a preferable user interface for an vet profile.
Figure 6:
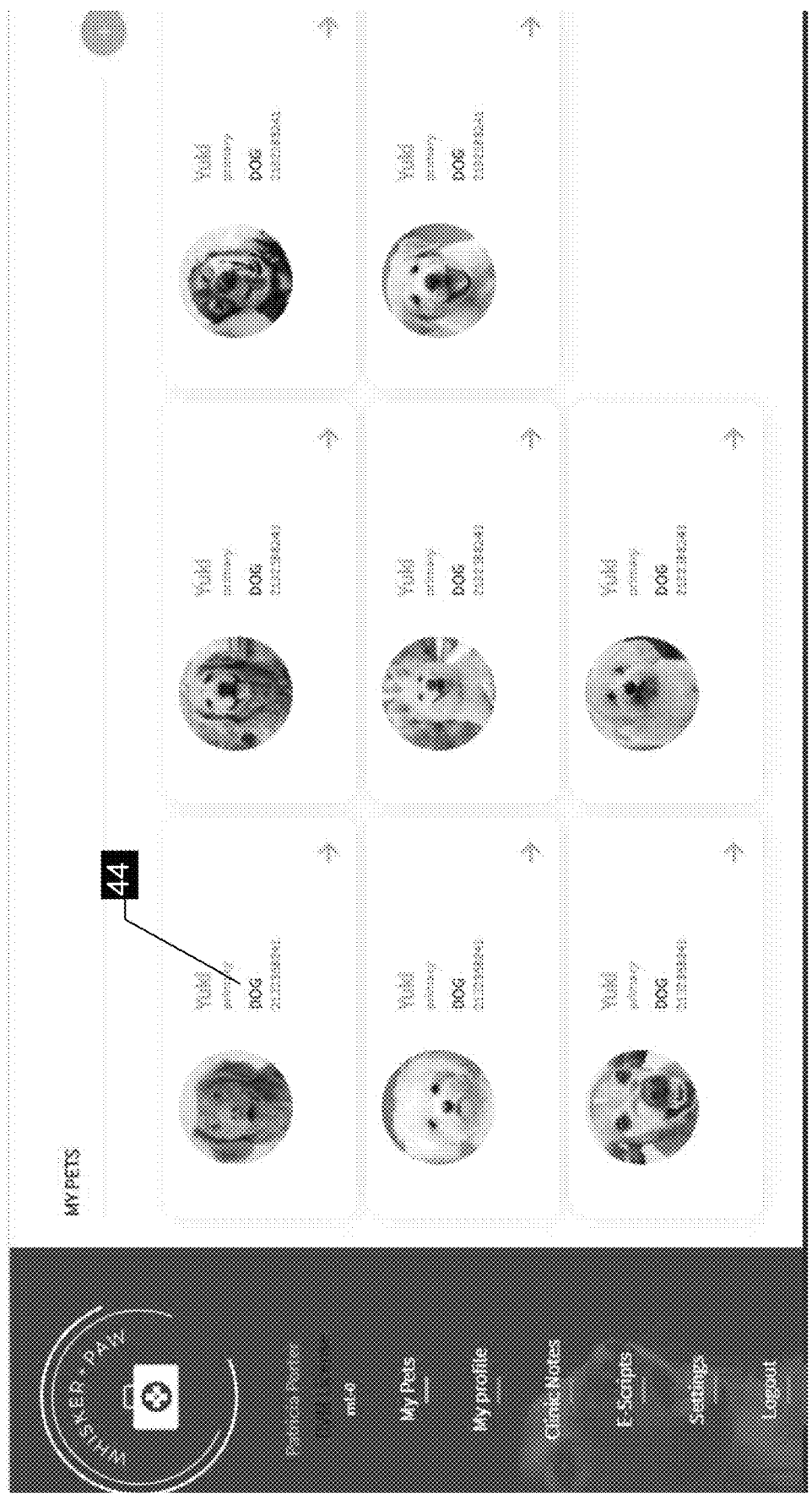
FIG. 6 is a preferable user interface for the vet and patient overview page.

FIGS. 5 and 6 show preferable user interfaces for a provider profile and the pet's overview page. Suitably, these pages of the platform pertain to the clinic, not the client. It is likely that a veterinarian will navigate to these pages immediately after the "DMV ready" button is pressed. In particular, FIG. 5 shows the provider's information. This contains specific provider information fields under the my info section 33 such as, name field 34, last name field 35, mobile field 36, and ssn field 37. FIG. 5 also shows the my bank info section 38. Under this section there are fields such as the name on account field 39, bank account number field 40, bank routing number field 41, and company field 42. Further disclosed, is a my licenses section 43 showing different licenses of the practitioner.

The my pets page shown in FIG. 6 may let providers navigate to each individual pet profile 44 to access medical history, vitals, and personal information, among other things. The provider may use these individual pet profiles 44 to access pertinent medical history regarding different pets during work. The my pets page of FIG. 6 is used to navigate from pet to pet as the veterinarian goes to different appointments as she is directed by the platform and "DMV ready" button.

Figure 7:
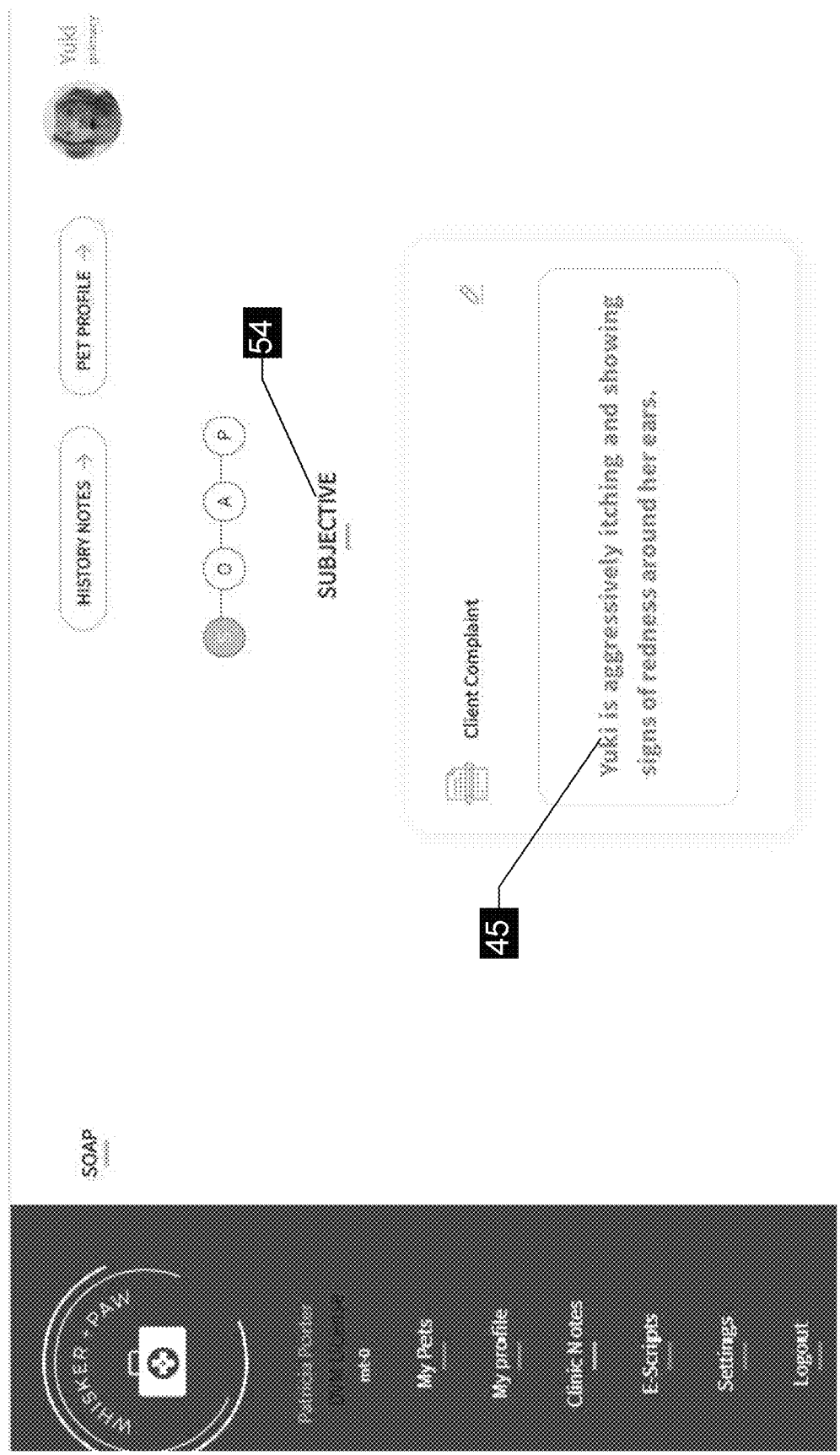
FIG. 7 is a preferable user interface for the SOAP notes, specifically the subjective notes.

After the "DMV ready" button is pressed, the veterinarian is alerted via the whiteboard that the pet is ready to be seen. The veterinarian may also review all of the notes and updates from nurse section, shown in FIGS. 3 and 4, made by the administrative staff. Then, the veterinarian enters exam room, and opens up SOAP Portal, which is disclosed in a preferred embodiment in FIGS. 7-10. The veterinarian may navigate to the "S" for subjective section 54, shown in FIG. 7, and asks the pet owner for the pet's chief complaint by saying, "So, why are you here today." Before he answers, the veterinarian can turn on a speech to text voice recognition button so that what the pet parent says populates the chief complaint field of the subjective section 45. The pet owner explains that the pet is itching and biting a specific part of the pet's body. The owner then says that the pet's body is also clearly aggravated there. After the owner is finished speaking, the veterinarian may press the analyze button on the screen. This action activates VEA's artificial intelligence and causes it to analyze what the owner said.

Figure 11:
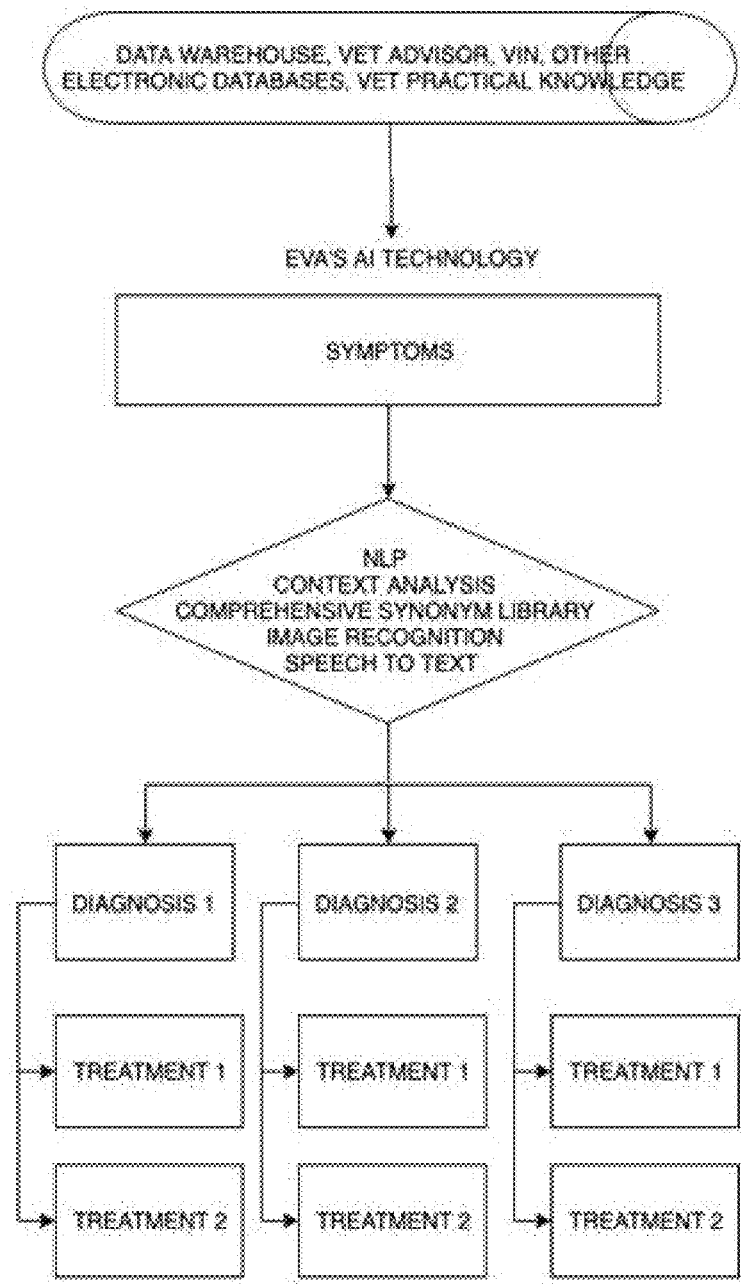
FIG. 11 is a flow chart showing VEA's AI process and methodology using symptom to diagnosis mapping as an example.

VEA's artificial intelligence process and methodology is shown in the flow chart in FIG. 11. VEA uses the API's such as natural language processing, context analysis, synonym engine, and voice analytics to turn what the pet owner said into a group of diagnoses. Now, hypothetical diagnoses populate the application screen, for example, "fleas, dermatitis, or hotspots." Next, VEA may map different treatment plans for the different diagnoses. When the veterinarian is satisfied with these results, she may press next.

Figure 8:
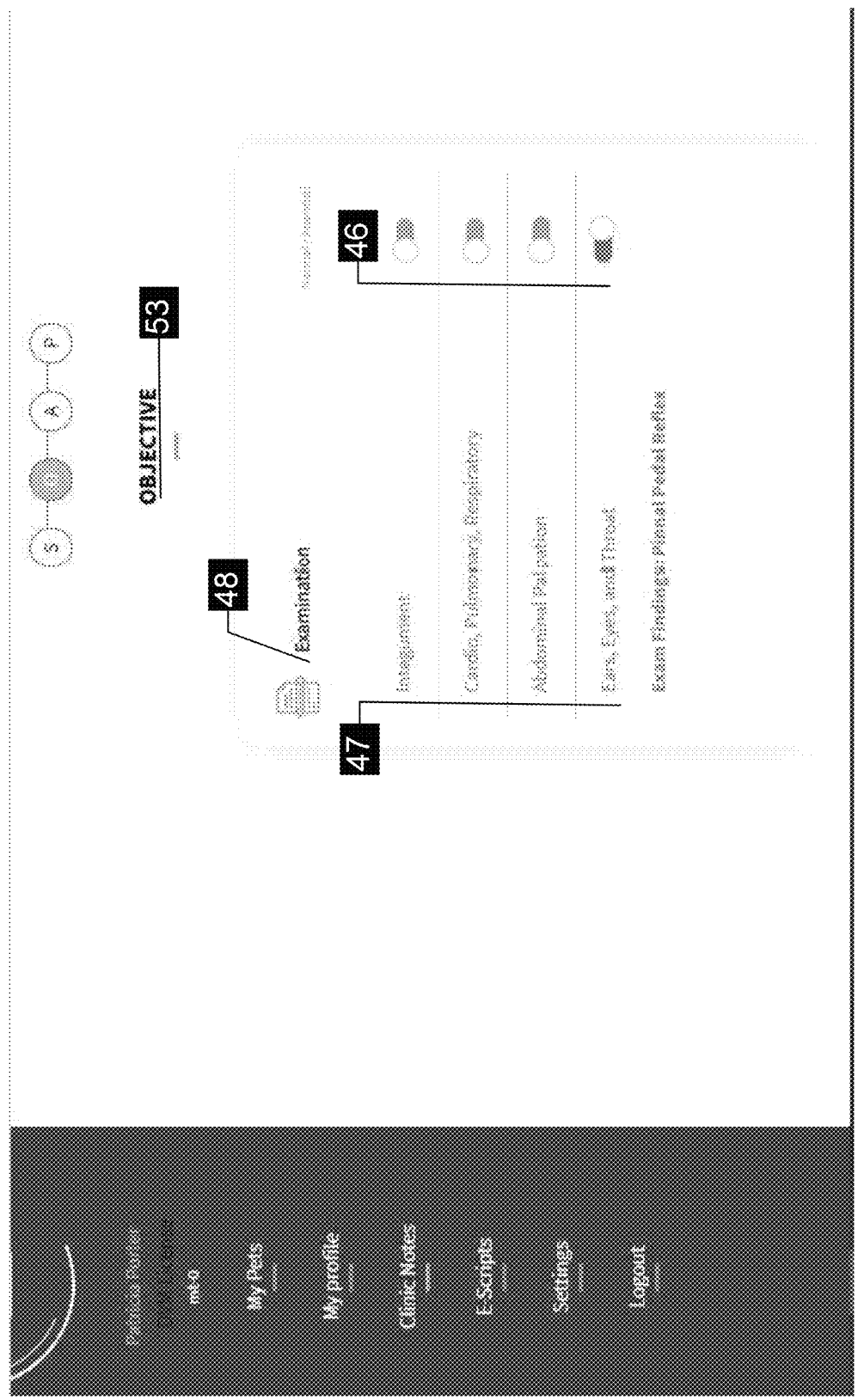
FIG. 8. Is a preferable user interface for the SOAP notes, specifically the objective notes.

Now, the veterinarian is on the "0" for objective section 53 of the SOAP notes, which is shown in a preferred embodiment by FIG. 8. In this section, there is an examination subsection 48 wherein the veterinarian may take notes using guided dropdowns and abnormality switches 46 for different examination criteria 47, such as ears, nose, and eyes, or abdominal palpation. The veterinarian completes the examination and may take the appropriate notes. The veterinarian may take the notes using dictation or with a digital keyboard. When she is finished, she may press next, prompting the next page to open.

Figure 9:
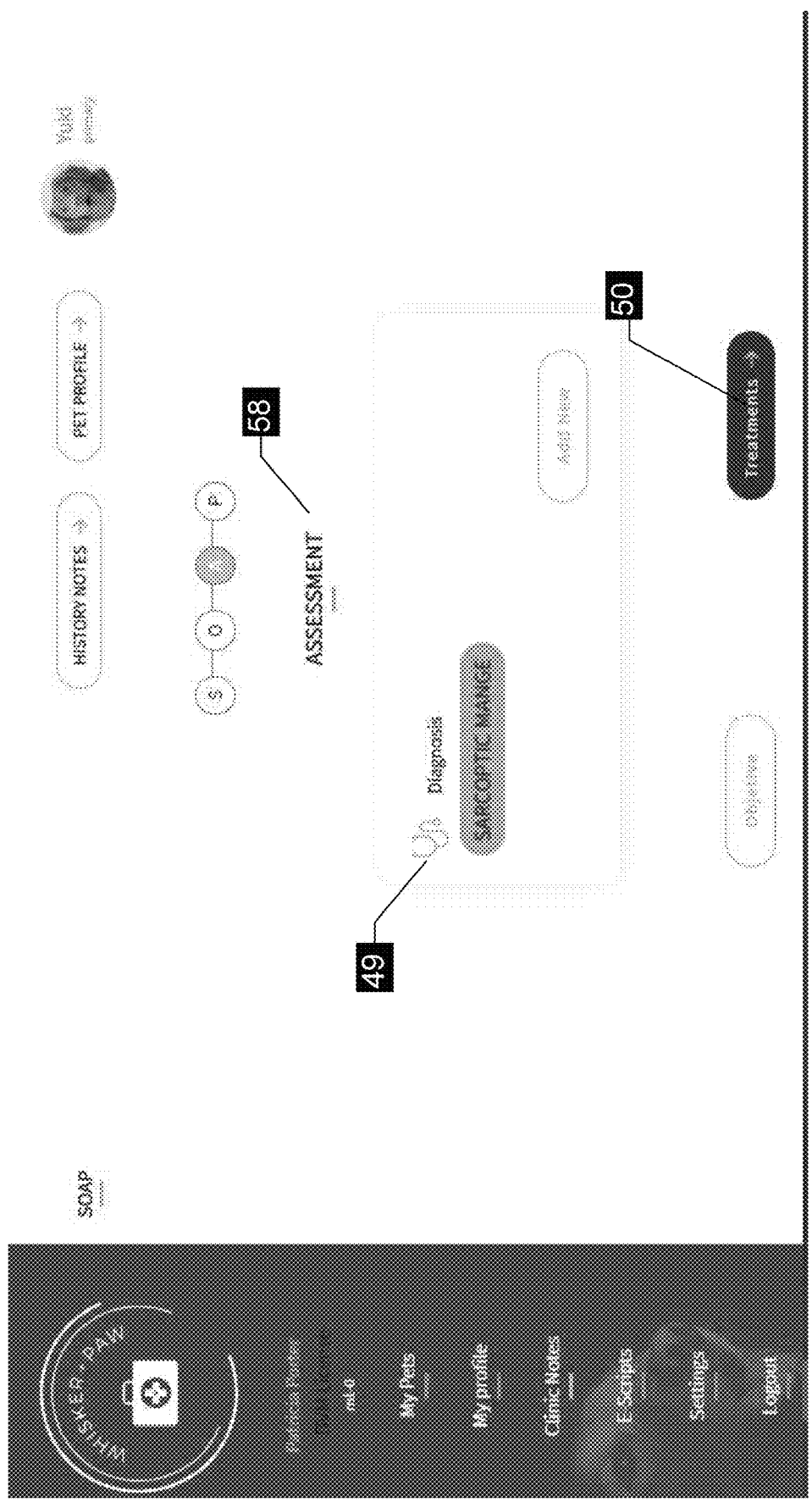
FIG. 9 is a preferable user interface the SOAP notes, specifically the assessment notes.

The veterinarian may now begin filling out the "A" or assessment section 58 of the SOAP notes which is shown in a preferred embodiment by FIG. 9. At this point, the differential diagnosis process begins to take place. The veterinarian can use this section to theorize which diagnoses she believes the pet could possibly have. In this section, the AI is prepopulating the results from the "S" or subjective section of FIG. 7. These prepopulated results can be found in the diagnosis subsection 49. This means the veterinarian can see the different diagnoses options, for example, "fleas, dermatitis, or hotspot." The most difficult step of differential diagnoses is likely done, because the veterinarian now has some examples of what the diagnosis could be, based on the common symptoms. The veterinarian can add or remove diagnosis, and she does. She then may press the treatments button 50, prompting the next page to open.

Figure 10:
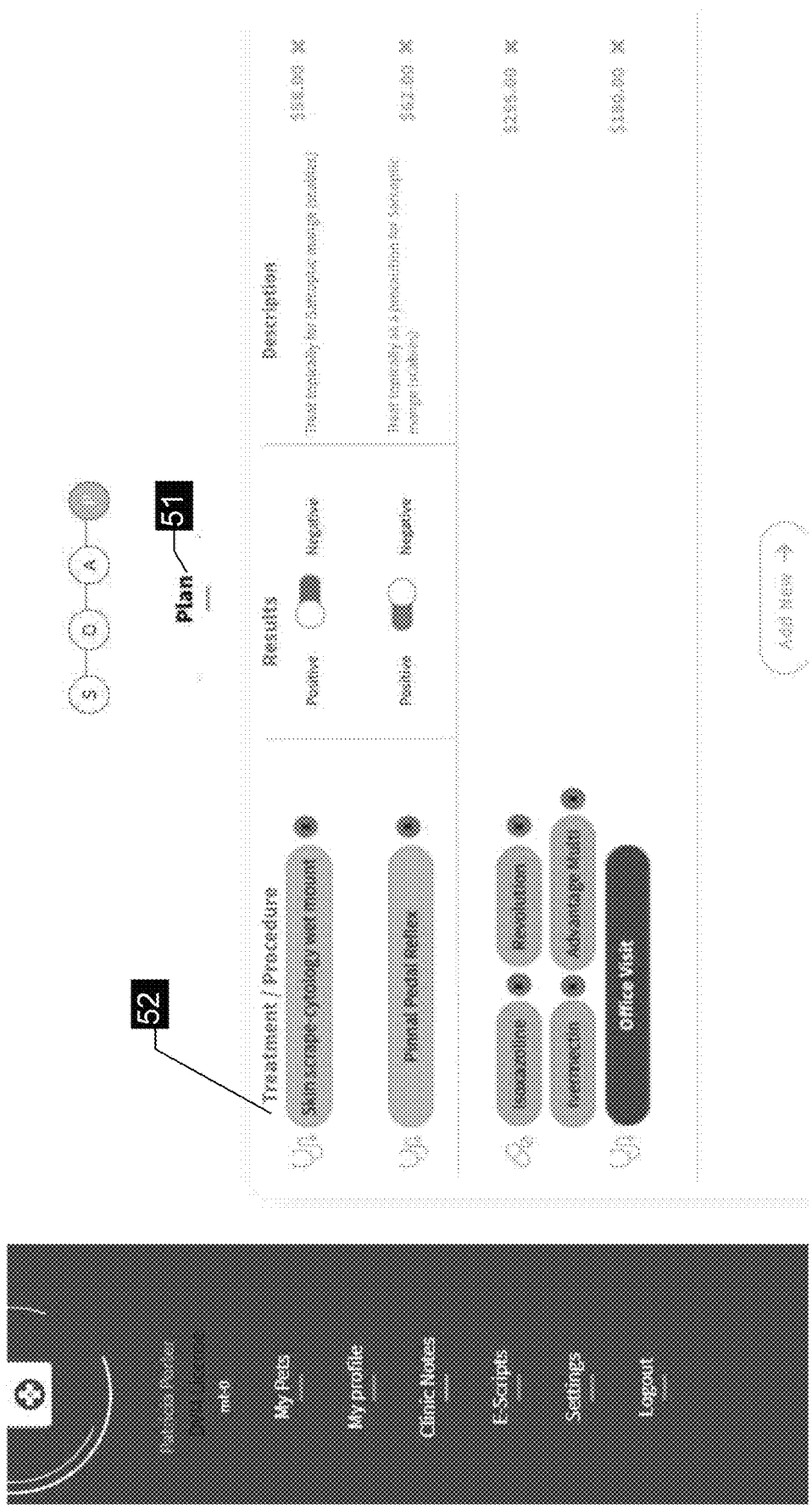
FIG. 10 is a preferable user interface the SOAP notes, specifically the plan notes.

The veterinarian is now on the "P" for plan section 51, as shown in FIG. 10. Here, under the treatment/procedure subsection 52, the veterinarian and the AI may build a treatment plan for the owner. The AI may map the treatments and diagnostics to the diagnosis that were selected from "A" or assessment section 58. Now, the pet owner can approve the selected treatments by signing-off on them within the application. Then the nurse or technician may be alerted via the whiteboard of the application that the pet is ready for treatment. Next, the pet owner is to be escorted to the waiting room.

Back in the exam room, the pet is treated and the veterinary technician may conduct various tests. When the results come in, the veterinary technician may pull up the lab section of the application and update the results. The results should be added to an addendum of the veterinarian's clinic notes with a date and timestamp. This may alert the veterinarian, via the whiteboard, that the pet is ready to see them again.

The veterinarian may confirm the diagnosis by entering a pin. Then she may finalize both the clinic notes, and the at-home treatment. The client signs off a final authorization if there is one and is prepared to complete the visit by paying. During this time VEA completes the visit notes and ascribes the proper medical billing codes automatically for the veterinarian. If the visit is covered by insurance, billing happens automatically.

Signing the final authorization may trigger another alert in the whiteboard that makes the clinic administrator aware that pet owner is ready to pay if the visit is not covered by insurance. The pet may then be taken to the waiting room by the veterinary technician. Then the veterinarian can explain the results to the pet owner. After everything is confirmed, the pet owner may pay. The owner may do this simply by paying through the application on their tablet or smartphone. If the visit is deemed to be covered by insurance, then billing has begun automatically. Billing codes are applied automatically for administrators prompting them to begin processing insurance claims. The application automatically connects care provided to treatments delivered, as shown in FIG. 10 under the plan subsection 51. Information relevant to the visit, such as, medical history, doctor notes, medication prescribed, medication instructions, and either claim status or total charges, may be made available in the application.

Figure 12:
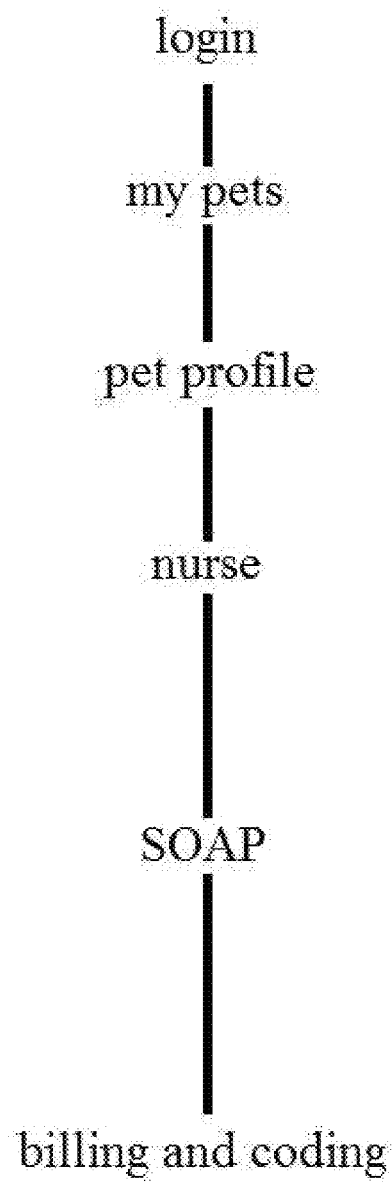
FIG. 12 is a flow chart showing a preferred embodiment of the path from one web page to another during the patient treatment process (Login→my pets→pet→profile→nurse-→SOAP→billing & coding).

FIG. 12 is a flow chart showing the one possible path from web page to web page during the patient treatment process. This is the same path that was followed in the aforementioned patient treatment process outlined above.

The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention. It should be apparent that further numerous structural modifications and adaptations may be resorted to without departing from the scope and fair meaning of the present invention as set forth hereinabove and as described herein below by the claims.

Although the method and apparatus is described above in terms of various exemplary embodiments and implementations, it should be understood that the various features, aspects and functionality described in one or more of the individual embodiments are not limited in their applicability to the particular embodiment with which they are described, but instead might be applied, alone or in various combinations, to one or more of the other embodiments of the disclosed method and apparatus, whether or not such embodiments are described and whether or not such features are presented as being a part of a described embodiment. Thus the breadth and scope of the claimed invention should not be limited by any of the above-described embodiments.

Terms and phrases used in this document, and variations thereof, unless otherwise expressly stated, should be construed as open-ended as opposed to limiting. As examples of the foregoing: the term "including" should be read as meaning "including, without limitation" or the like, the term "example" is used to provide exemplary instances of the item in discussion, not an exhaustive or limiting list thereof, the terms "a" or "an" should be read as meaning "at least one," "one or more," or the like, and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that might be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases might be absent. The use of the term "assembly" does not imply that the components or functionality described or claimed as part of the module are all configured in a common package. Indeed, any or all of the various components of a module, whether control logic or other components, might be combined in a single package or separately maintained and might further be distributed across multiple locations.

We claim:

1. An web application defined by program code on computer readable memory, wherein the program code is configured to:

store a plurality of health records in a database;
allow a medical practitioner to input and store a plurality of new health records in the database, wherein the database includes a health record of a pet;
allow the medical practitioner to take a plurality of medical notes via providing a SOAP portal with:
i. an "S" link configured to display a "subjective" labeled user interface (54) which displays an input box (45) for data entry to the database of information relayed to the medical practitioner by the pet's owner or caretaker along with an association to a health record of the pet;
ii. an "O" link configured to display an "objective" labeled user interface (53) which displays at least one examination criteria (47) associated with an abnormality switch (46) for data entry to the database of an "abnormal" or "normal" indication relative to an examination criteria with an association to the heath record of the pet;
iii. an "A" link configured to display an "assessment" labeled user interface (58) which displays at least one diagnoses of a condition, wherein the diagnosis is presented on a data entry button (49) for data entry to the database of the diagnosis with an association to the pet's health record;
iv. a "P" link configured to display an "plan" labeled user interface (51) which displays at least one treatment or procedure, wherein the treatment or procedure is presented on a data entry button (52) for data entry of the treatment or procedure to the database with an association to the pet's health record, wherein the treatment or procedure is associated with a positive or negative switch for data entry to the database of a data related to a positive or negative result of the treatment or procedure with an association to the pet's health record;
distribute the health records deliberately to a client, an administrator, or a practitioner;
integrate a patient tracking system with the health records;
employ an artificial intelligence software known as the veterinarian's electronic assistant or VEA;
employ a database containing the identity of a plurality of diagnoses of a condition associated with at least one symptom so that at least one of the diagnoses of a condition same can be presented on the data entry button (49) whenever an associated symptom is entered by the medical practitioner into input box (45).

2. The artificial intelligence of claim 1 wherein the program code is further configured to:
receive information about a plurality of symptoms via a natural language process;
connect symptoms to a plurality of diagnoses and a plurality of treatment plans;
summarize a plurality of findings;
distribute and display this information to a plurality of medical practitioners, administrators, and clients.

3. The web application of claim 1 wherein the program code is further configured to:
integrate a plurality of known software for billing, scheduling, and calendaring;
allow a client to pay a medical bill in the web application;
allow a administrator to submit a insurance claim;
allow a client and administrator to share a calendar.

4. The patient tracking system of claim 1 wherein the program code is further configured to:
allow the system to be interactive;
prompt a practitioner to complete steps of a patient care process;
alert a member of the patient care process to take an action;
display the status of the patient.

5. The web application of claim 1 wherein the program code is further configured to:
automate claims processing, medical billing, and billing coding, wherein the claims are automated via the program receiving information about a plurality of diagnoses via a natural language process and connecting diagnoses to a plurality of ICD-10 Diagnostics and their Diagnostic Codes and a plurality of superbills for final billing to the insurance companies for payment;
distribute and display this information to a plurality of business administrators, insurance payor groups, and claims processing specialists.

6. The web application of claim 1 wherein the program code is further configured to:
allow the medical practitioner to take a note using a SOAP note methodology.

7. A method of discerning between a differential diagnosis using an artificial intelligence software while taking a plurality of SOAP method notes comprising the steps of:
(a) operating a web application defined by program code on computer readable memory, wherein the program code is configured to:
store a plurality of health records in a database;
allow a medical practitioner to input and store a plurality of new health records in the database, wherein the database includes a health record of a pet;
allow the medical practitioner to take a plurality of medical notes via providing a SOAP portal with:
v. an "S" link configured to display a "subjective" labeled user interface (54) which displays an input box (45) for data entry to the database of information relayed to the medical practitioner by the pet's owner or caretaker along with an association to a health record of the pet;
vi. an "O" link configured to display an "objective" labeled user interface (53) which displays at least one examination criteria (47) associated with an abnormality switch (46) for data entry to the database of an "abnormal" or "normal" indication relative to an examination criteria with an association to the heath record of the pet;
vii. an "A" link configured to display an "assessment" labeled user interface (58) which displays at least one diagnoses of a condition, wherein the diagnosis is presented on a data entry button (49) for data entry to the database of the diagnosis with an association to the pet's health record;

viii. a "P" link configured to display an "plan" labeled user interface (51) which displays at least one treatment or procedure, wherein the treatment or procedure is presented on a data entry button (52) for data entry of the treatment or procedure to the database with an association to the pet's health record, wherein the treatment or procedure is associated with a positive or negative switch for data entry to the database of a data related to a positive or negative result of the treatment or procedure with an association to the pet's health record;

employ an artificial intelligence software known as the veterinarian's electronic assistant or VEA;

employ a database containing the identity of a plurality of diagnoses of a condition associated with at least one symptom so that at least one of the diagnoses of a condition same can be presented on the data entry button (49) by operation of the VEA whenever an associated symptom is entered by the medical practitioner into input box (45);

(b) entering a symptom into the web application via the input box (45);

(c) allowing the artificial intelligence software to match the symptoms to at least one diagnoses in the database containing the identify of a plurality of diagnoses of a condition associated with a system;

(d) processing and displaying this information, via the web application, to the medical practitioner on command button (49);

making corrections to the diagnoses to increase future accuracy of the artificial intelligence software; and, explaining a plurality of diagnoses and treatment plans to the pet's owner.

8. The method of claim 7 wherein the artificial intelligence software uses a dynamic database comprised of information from a Veterinary Advisor textbook and a veterinary practical knowledgebase.

9. The method of claim 8 wherein the artificial intelligence software is outfitted with a plurality of API's such as a context analysis API, a comprehensive synonym library API, a speech to text API, and a natural language process API.

10. The method of claim 9 wherein the artificial intelligence software maps diagnoses to treatment.

11. The method of claim 10 wherein the artificial intelligence software is active during a subjective section and a plan section of the SOAP method notes.

12. The method of claim 10 wherein the step of explaining a plurality of diagnoses and treatment plans to the pet's owner is accomplished programmatically via production to the pet's owner of a text summary of said diagnoses and treatment plans.

* * * * *